United States Patent [19]

Brendl et al.

[11] Patent Number: 4,697,802
[45] Date of Patent: Oct. 6, 1987

[54] X-RAY DIAGNOSTICS INSTALLATION INCLUDING A TILTING TABLE

[75] Inventors: Rudolf Brendl; Alfred Hahn, both of Erlangen; Karl Weiss, Buckenhof, all of Fed. Rep. of Germany

[73] Assignee: Siemens Aktiengesellschaft, Berlin and Munich, Fed. Rep. of Germany

[21] Appl. No.: 946,922

[22] Filed: Dec. 29, 1986

[30] Foreign Application Priority Data

May 5, 1986 [DE] Fed. Rep. of Germany ....... 3615187

[51] Int. Cl.$^4$ ............................................. A61G 13/00
[52] U.S. Cl. .................................................... 269/323
[58] Field of Search ................ 269/322, 323; 378/209; 108/4–8

[56] References Cited

U.S. PATENT DOCUMENTS 2,038,327 4/1936 Wantz .
3,379,877 4/1968 Makino et al. .

FOREIGN PATENT DOCUMENTS 0146006 6/1985 European Pat. Off. .

OTHER PUBLICATIONS

Siemens Brochure, "Explorator 35".

*Primary Examiner*—Robert C. Watson
*Attorney, Agent, or Firm*—Hill, Van Santen, Steadman & Simpson

[57] ABSTRACT

At its outside, the table frame or support is provided with two symmetrical, circular drive paths into each of which a drive wheel engages. Two respective guide rails are arranged at the table frame or support at both sides thereof, two respective, stationary guide pegs engaging into these guide rails in the horizontal position, said guide rails being fashioned and directed or, respectively, curved such that, given adjustment of the tilting table out of the horizontal position, respectively two guide pegs leave their guide rail and the lower end of the table frame or support is lifted to such a degree that it lies above the floor level. The curvature of at least one pair of guide rails at both sides of the table frame or support is selected such that the tilting speed is roughly uniform.

3 Claims, 3 Drawing Figures

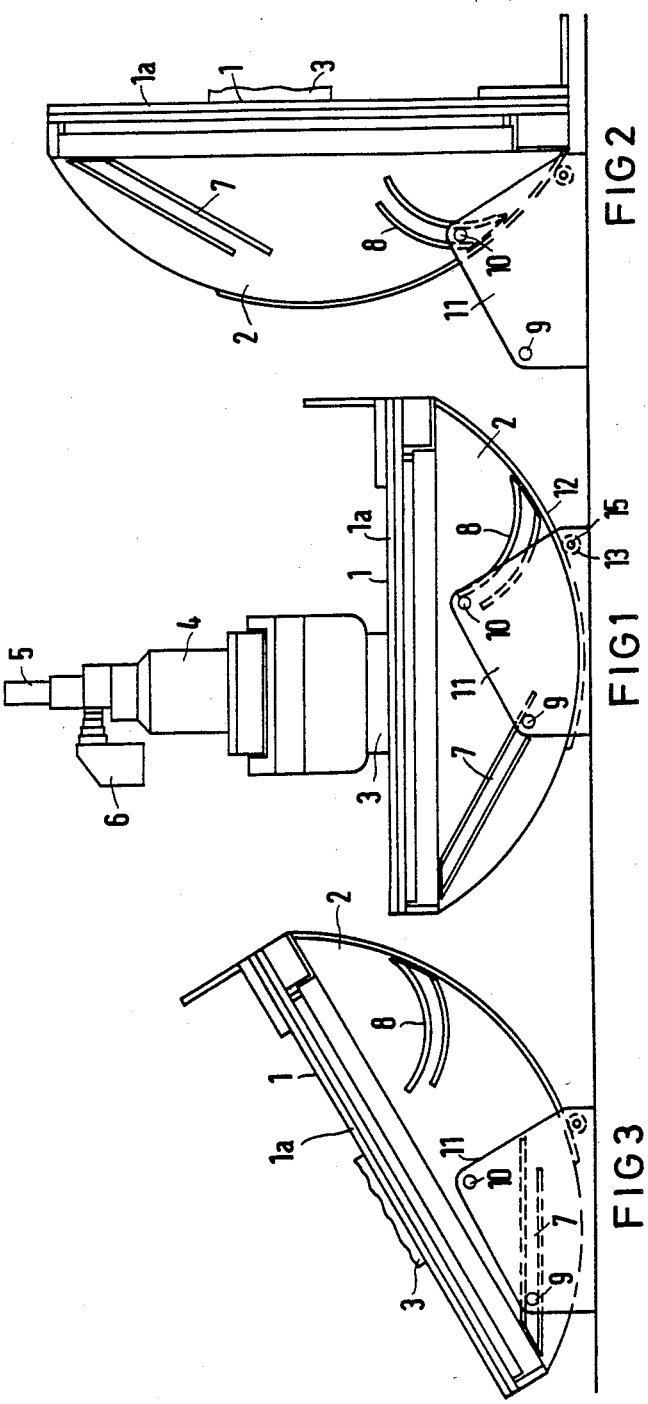

X-RAY DIAGNOSTICS INSTALLATION INCLUDING A TILTING TABLE

BACKGROUND OF THE INVENTION

1. Field of the Invention

The invention relates to an x-ray diagnostics installation including a tilting table which is tiltable toward both sides from the horizontal position, by 90° toward one side thereof, wherein the tilting table is secured to a table frame or support which is provided with circular drive paths at its outside, a drive wheel engaging thereinto, and whereby two guide rails are provided at the table frame or support at each side, two stationary guide pegs engaging thereinto in the horizontal position and said guide rails being fashioned and directed such that, given adjustment of the tilting table out of the horizontal position, respectively one guide peg leaves its guide rail and the lower end of the table frame or support is raised to such a degree that it lies above the floor level.

2. Description of the Prior Art

Given low structural outlay, an x-ray diagnostics installation of this type allows a tilting motion of, for example, 90° toward the one side of the horizontal position and of 30° toward the other side. In a known x-ray diagnostics installation of this type, the guide rails are fashioned straight, so that the tilting speed varies given constant speed of the tilting motor.

SUMMARY OF THE INVENTION

An object of the invention is to improve an x-ray diagnostics installation of the type described above such that an essentially uniform tilting speed derives.

This object is achieved in accord with the invention in that the guide rails allocated to the foot end are curved toward the table top. Even on the basis of a circular curvature around a point lying close to the foot end of the table top, a roughly uniform tilting speed is thereby obtainable given a constant speed of the tilting motor. An exactly uniform tilting speed can be achieved by a corresponding curve shape.

BRIEF DESCRIPTION OF THE DRAWINGS

The invention shall be set forth in greater detail below with reference to an exemplary embodiment shown in the drawing. Shown therein are:

FIG. 1 is an x-ray diagnostics installation of the invention in a side view.

FIG. 2 is an x-ray diagnostics installation of FIG. 1 in a head-up 90° tilted position.

FIG. 3 is an x-ray diagnostics installation of FIG. 1 in a head-down tilted position.

DESCRIPTION OF THE PREFERRED EMBODIMENTS

The installation according to FIG. 1 includes a tilting table 1 which is seated longitudinally displaceable on a table frame or support 2 in motor-driven fashion. An x-ray tube (not shown) lies under the tilting table 1, this tube being secured to a carrier 3 which carries an x-ray image intensifier 4 above the tilting table 1, this x-ray image intensifier 4 includes a following video camera 5 and a sheet film camera 6. In the horizontal position of the tilting table 1 shown in FIG. 1, the table frame or support 2 has guide rails (of which the guide rails 7, 8 are visible in FIG. 1) engagable around on guide pegs of which the guide pegs 9, 10 are visible in FIG. 1. The guide pegs 9, 10 are secured to stationary bearing parts arranged laterally at the table frame or support 2, the bearing part 11 thereof being visible in FIG. 1.

At its outside, the table frame or support 2 is provided with two arcuate drive paths of which the drive path 12 is shown in FIG. 1. A gear wheel 13 that can be turned by a motor is in engagement with the drive path 12 fashioned as a chain.

Parts corresponding to the parts 7 through 13 which are not visible are symmetrically arranged at the installation, i.e. a respective drive path corresponding to 12, a drive wheel corresponding to 13, two guide rails corresponding to 7, 8 and two guide pegs corresponding to 9, 10 are symmetrically present at both apparatus sides.

When the tilting table 1 is to be raised from its horizontal position in which the table frame or support 2 has the guide rails 7, 8 supported on the guide pegs 9, 10 into a vertical position, i.e. is to be rotated by 90°, then the drive motor is switched on, this turning a shaft 15 and, thus, the drive wheel 13. The table frame or support 2 including the tilting table thereby moves in a clockwise direction and the guide pegs 9 leave the guide rails 7. In this tilting motion, consequently, the table frame or support 2 then rests on the guide pegs 10 only by means of the guide rails 8. What is achieved by the guidance of the guide pegs 10 in the guide rails 8 is that the tilting table 1 is raised into the position shown in FIG. 2 without having its lower end strike the floor.

When the tilting table 1 is to be pivoted out of its horizontal position shown in FIG. 1 in a counter-clockwise direction (FIG. 3), then the guide pegs 10 leave the guide rails 8 in an analogous way and the guidance ensues by means of the guide pegs 9 in the guide rails 7. The drive wheels 13 thereby turn opposite their rotation in the raising into the position of FIG. 2. The table frame or support 2 is thereby pivoted together with the tilting table 1 in a counter-clockwise direction into the low head-end position shown in FIG. 3 in which the tilting table 1 describes an angle of about 30° with the floor.

When adjusting the tilting table 1 out of the horizontal position of FIG. 1 into the final positions of FIGS. 2 and 3, accordingly, respectively one of the guide pegs 9, 10 leaves its guide path 7, 8 and the respective end of the apparatus closer to the floor is raised to such degree that it lies above the floor level, whereby the table frame or support is carried by the respective guide pegs 9, 10 in the guide rails 7, 8.

It follows from FIGS. 1 through 3 that the guide rails 8 lying close to the foot end of the table top 1a are curved around a point which lies close to this foot end. The curvature is that of a circular arc. What is thereby achieved is that, given constant speed of the drive motor, a roughly uniform tilting speed derives when tilting by 90°. The tilting speed is thereby exactly uniform when a suitable curve shape of the guide rails 8 is selected.

As is apparent from the foregoing specification, the invention is susceptible of being embodied with various alterations and modifications which may differ particularly from those that have been described in the preceding specification and description. It should be understood that we wish to embody within the scope of the patent warranted hereon all such modifications as reasonably and properly come within the scope of our contribution to the art.

We claim as our invention:

1. An x-ray diagnostics installation including a tilting table which is tiltable toward both sides out of the horizontal position, by 90° toward one side thereof, wherein said tilting table is secured to a table frame or support which is provided with arcuate drive paths at its outside, a drive wheel engaging thereinto, and whereby two guide rails are arranged at said table frame or support at each side thereof, two stationary guide pegs engaging into said guide rails in the horizontal position and said guide rails being fashioned and aligned such that, given adjustment of said tilting table out of said horizontal position, respectively one guide peg leaves its guide rail and the lower end of said table frame or support is raised to such degree that it lies above the floor level, comprising the improvement that the guide rail allocated to the foot end is curved toward a top of the table.

2. An x-ray diagnostics installation according to claim 1, wherein said curved guide rail is circularly curved around a point lying close to said foot end of said table top.

3. An x-ray diagnostics installation according to claim 1, wherein said curved guide rail is curved such that the tilting speed of said table is exactly uniform given a constant rotational speed of said drive wheel.

* * * * *